Figure 1:
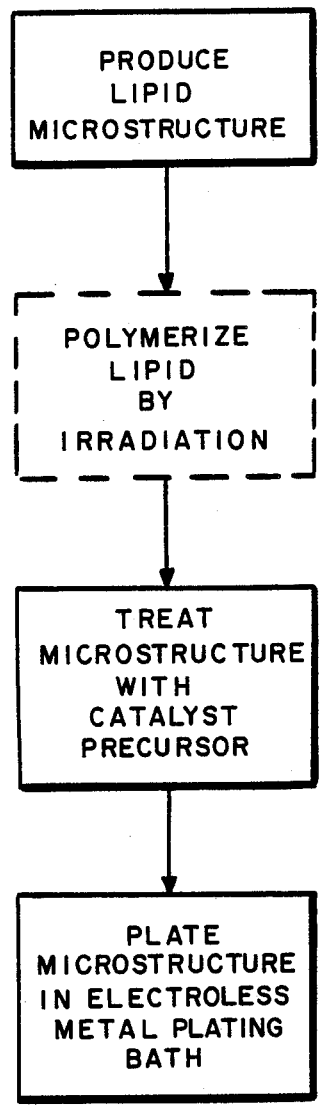

United States Patent [19]

Schnur et al.

[11] Patent Number: 4,911,981
[45] Date of Patent: Mar. 27, 1990

[54] METAL CLAD LIPID MICROSTRUCTURES

[76] Inventors: Joel M. Schnur, 6009 Lincolnwood Ct., Burke, Va. 22015; Paul E. Schoen, 5006 Taney Ave., Alexandria, Va. 22304; Paul Yager, 208 10th St., S.E., Washington, D.C. 20003; Jeffrey M. Calvert, 6033 Wilmington Dr., Burke, Va. 22015; Jacque H. Georger, 8409 Great Lake Rd., Springfield, Va. 22153; Ronald Price, P391 Mear's Point Marina, Graysonville, Md. 21638

[21] Appl. No.: 63,029

[22] Filed: Jun. 16, 1987

[51] Int. Cl.$^4$ .................. C23C 18/30; B32B 15/08; B32B 15/01; H01B 1/00
[52] U.S. Cl. .................. 428/402.24; 428/371; 428/389; 523/137; 523/222; 252/513; 524/440
[58] Field of Search ............... 428/402.24, 402.2, 371, 428/389; 523/137, 222; 252/513; 524/440

[56] References Cited

U.S. PATENT DOCUMENTS

| | | | |
|---|---|---|---|
| 3,014,818 | 12/1961 | Campbell | 252/513 X |
| 3,318,697 | 5/1967 | Shrewsbury | 430/138 X |
| 3,528,809 | 9/1970 | Farnand et al. | 419/5 |
| 4,098,945 | 7/1978 | Oehmke | 252/513 X |
| 4,663,240 | 5/1987 | Hajdu et al. | 523/137 X |
| 4,704,413 | 11/1987 | Nabeta et al. | 523/137 |

OTHER PUBLICATIONS

McRae, Wayne A., "Electroless Plating", in: Kirk-Othmer Encyclopedia of Chemical Technology (3rd ed.), vol. 8, pp. 738-750.

Schoen et al., "Order in Diacetylenic Microstructures", Mol. Cryst. Liq. Cryst., vol. 153, (Dec. 1987), pp. 357-366.

Georger et al., "Helical and Tubular Microstructures Formed by Polymerizable Phosphatidylcholines", J. Am. Chem. Soc., vol. 109, (Sep. 1987), pp. 6169-6175.

Schnur et al., "Lipid-Based Tubule Microstructures", Thin Solid Films, vol. 152 (Sep. 14, 1987), pp. 181-206.

Primary Examiner—John F. Terapane
Assistant Examiner—Gary L. Geist
Attorney, Agent, or Firm—Wolf, Greenfield & Sacks

[57] ABSTRACT

Tubular, spheroidal, and helical lipid microstructures are individually clad with a metal coat deposited on the microstructures by an electroless plating bath. In metal cladding the microstructures, the surfaces of the lipid microstructures are sensitized by adsorption thereon of a catalytic precursor which enables metal from the electroless plating bath to deposit upon and adhere to the sensitized surface. The metal plate is electrically conductive and may also be magnetic. A composite material is produced by embedding the metal clad microstructures in a matrix of a polymer such as an epoxy or a polyurethane.

24 Claims, 1 Drawing Sheet

METAL CLAD LIPID MICROSTRUCTURES

U.S. GOVERNMENT RIGHTS IN THE INVENTION

This invention was made jointly by three employees of the Naval Research Laboratory, Washington, D.C. and three employees of Geo-Centers, Inc. The three Geo-Centers employees, at the time the invention was made, were in the performance of work under Naval Research Laboratory's contract N00014-85-C-2243 with Geo-Centers. The United States of America has certain rights in the invention arising out of that contract, including a nonexclusive, nontransferable, irrevocable, paid-up license to practice the invention or have it practiced for or on behalf of the United States throughout the world. The United States of America may also have rights in the invention derived from the three employees of the Naval Research Laboratory who are joint inventors of this invention.

FIELD OF THE INVENTION

This invention relates in general to the production of individual lipid microstructures each of which is covered by its own adherent metal coat. More particularly, the invention pertains to the production of metal coated lipid microstructures which are in the form of a hollow cylinder or in the form of a helix or in the form of a sphere.

BACKGROUND OF THE INVENTION

It is known that phospholipids which possess a diacetylenic functional group in each of two fatty acid chains, e.g. 1, 2-bis (10,12-ticosadiynoyl)-sn-glycero-3-phosphocholine ($DC_{23}PC$), self-assemble to form a variety of microstructures under certain well defined conditions in agueous solutions.

Vesicles are spheroidal structures in which one or more lipid bilayers are wrapped in a lamellar fashion to enclose a volume of solution. Vesicles range in size from approximately 50 nanometers (a nanometer is a billionth of a meter) to 25 microns (a micron is a millionth of a meter). These structures are also formed by non-diacetylenic lipids. The vesicles used in this invention were prepared in the manner described in a monograph by Paul Yager and Paul E. Schoen in the "Journal of Molecular Crystals And Liguid Crystals", vol. 106, pp 371-381 (1984).

Tubules are hollow, cylindrical structures composed of up to approximately ten bilayers; characteristic diameters are 0.2 to 3.0 microns, wall thicknesses are approximately 5 to 50 nanometers. Tubule length is a controllable parameter, based on fabrication procedure. The aspect ratio (ratio of length to radius) is therefore also controllable.

Preparation of tubules for this invention was accomplished by two methods. The first method involved raising the temperature of an aqueous vesicular dispersion above the chain melting temperature, $T_m$, of the diactylenic lipid (43° C. for $DC_{23}PC$) followed by slow cooling to just below $T_m$ as described in "Polymer Preprints", by A. Sinqh and J. Schnur, vol. 26, pp 184-185, (1986), in the above cited "Journal of Molecular Crystals and Liquid Crystals" monograph, and in U.S. Pat. Application No. 852,596, which was filed on April 16, 1986 now abandoned on an invention by Paul Schoen, Paul Yager, and Joel Schnur in Lipid Tubules. The structures thus formed are referred to as "thermally-grown tubules". In the second procedure, a non-solvent such as water is added to a solution of the diacetylenic lipid in an organic solvents such as an alcohol, until the solubility of the material in the mixed medium is exceeded and precipitation occurs. Such structures are referred to as "solvent grown tubules".

Helices are spiral-shaped structures that are also produced by the tubule formation methods described above. The helical structures have a pitch of about one micron and are typically one or two bilayers thick. The diameters of the helices are comparable to those of the tubules.

The diacetylenic lipid microstructures are known to undergo free-radical topotactic polymerization upon exposure to photons or electrons of sufficient energy, such as can be produced by ultraviolet (UV) radiation, by X-rays, by gamma rays, and by an electron beam. The integrity of the resultant polymeric microstructures is improved over their monomeric analogues in regard to thermal, chemical, and mechanical stability. In one utilization of this invention, diacetylenic microstructures were polymerized as a dispersion in aqueous alcohol (ethanol/water=20/80 v/v) at 0° C. by exposure to 1.33 Mev $^{60}Co$ gamma radiation at dosages of 6 to 9 Mrad.

The lipid microstructures referred to above are electrical insulators and those microstructures have weak diamagnetic susceptibility—that is, the lipid microstructures can be aligned only by a strong ($2 \times 10^4$ gauss) magnetic field and have poor electrical conductivity.

PRINCIPAL OBJECT OF THE INVENTION

The principal object of the invention is the production of lightweight, rugged, electrically conductive individual microstructures (which can also be magnetic) by the adhesion of a thin metal coat to those individual microstructures.

THE DRAWING

FIG. 1 is a flow diagram showing the steps for performing the procedures disclosed herein for producing metal clad lipid microstructures. The step indicated in the broken line box is an optional step that may be omitted.

THE INVENTION

Essential to the production of the metal coated lipid microstructures is the adaptation of the electroless metal plating procedures that were developed for metalization of electrical insulators of the kind used as substrates in printed circuitry. For review of electroless metal plating procedures, see the article by C. R. Shipley, Jr., in "Plating And Surface Finishing", Vol. 71, pp 92-99, (1984). In the performance of an electroless metal plating procedure, the insulative surface of the substrate must be sensitized to enable plating to occur. A number of different procedures are known for sensitizing the surface of insulative substrates. Some of those procedures involve conditioning the surface by mechanical abrasion or by etching the surface with strong acids or bases. Most of the sensitizing procedures cannot be employed to sensitize lipids without damaging the lipid microstructures.

In the practice of this invention, the lipid microstructures are sensitized by the attachment of a catalyst precursor to the surfaces of the lipid microstructures. That catalyst precursor preferably is palladium but can be of other materials, such as platinum or gold. More specifically, it is preferred to sensitize the lipid microstructure by attachment of a palladium/tin (Pd/Sn) colloidal catalyst precursor to the surface of the lipid microstructure. Once the catalytic precursor is attached to the lipid microstructure, the remainder of the electroless metal plating procedure is straightforward.

The metal coatings produced by the procedures disclosed herein can consist, but are not limited to, electroless nickel and electroless copper. The nickel coat produced by an electroless Ni plating bath is actually an alloy of nickel and phosphorus of varying composition. An alkaline nickel plating bath produces a nickel alloy having approximately 3% phosphorus. That alloy has a dc electrical conductivity of between $1.0 \times 10^4$ and $1.7 \times 10^4$ mho/cm and magnetic susceptibility of 30 oersteds. An acid electroless nickel plating bath produces a nickel alloy having approximately 12% phosphorus. The dc electrical conductivity of the high phosphorus content alloy is similar to that of the alloy of low phosphorus content, but the high phosphorus alloy is essentially non-magnetic as discussed in the above cited monograph of C. R. Shipley, Jr.

The metal deposit produced by electroless copper plating bath is essentially entirely of elemental copper. The dc electrical conductivity of the copper metal deposit is $6.0 \times 10^5$ mho/cm and is non-magnetic.

The metal coatings produced on the lipid microstructures are reasonably uniform and continuous. The metal layers are of controllable thickness, typical ranging between about 20 nm to 100 nm. After the initial metal coat has been formed on the lipid microstructure, the coat can be covered with other materials (such as different metals) to increase its thickness or to alter its surface characteristics. The metalization procedures disclosed herein are substantially compatible with the chemical and mechanical constraints of the lipid microstructures so that the morphology of the microstructure is preserved.

Advantages of the procedures disclosed herein are that they mainly involve inexpensive reagents and do not require complicated or expensive processing equipment. Further, the procedures present only minimum safety hazards inasmuch as they are principally concerned with agueous solutions and do not produce environmentally unacceptable residues or wastes.

UTILITY OF METAL CLAD LIPID MICROSTRUCTURES

Among the many ways of utilizing the metal clad microstructures, one of the most important is the use of the microstructures as electrical components in microcircuits that otherwise could not be built. The helical microstructures provide electrical inductors. The tubules can be used as capacitors by coating the inside and outside surfaces with metal. The tubules may serve as resistors or as low loss electrical connectors, depending upon the properties of the metal coated on the tubules. The microstructures can be utilized as adjuncts to semiconductor microcircuits in locations where it is difficult to provide inductance or capacitance.

Nickel clad ferromagnetic tubules and tubules clad with other magnetic metals may be used in display devices by suspending the tubules n a medium that permits the tubules to turn under the control of a magnetic field.

Copper clad tubules and tubules clad with other nonmagnetic metals may be used in display devices by controlling the orientation of those tubules through fluid flow. The optically opaque tubules, for example, can be brought into alignment by a flowing fluid.

The metal clad microstructures, particularly the tubules and helices, are useful in polymeric and other structural materials as replacements for or in addition to the glass fibers and graphite fibers now used as reinforcing materials. In such applications, the lightweight microstructures, especially the helices, can be effective in improving the mechanical properties of the composite material and the metal clad microstructures can provide electrical conductivity in the composite that is similar to the graphite's conductivity.

Metals such as palladium, platinum, and nickel are well-known for their capacity to store molecular hydrogen in the form of metal hydrides. The high surface area to weight ratio of hollow nickel, platinum, and palladium clad tubules makes those tubules useful for the storage and safe transportation of hydrogen.

Another way of usefully employing microstructures clad for example, with magnetic metals such as nickel or cobalt, is to implant those metal clad microstructures in tumors by injection through a needle or catheter or by drawing the microstructures to the desired site with a magnet that is outside the body. The minute size of the microstructures allows better control of the distribution of the magnetic material within the tumor than is feasible with the coarser magnetic particles now available. Hyperthermia can be induced in the tumor by employing an alternating magnetic field to produce eddy currents in the magnetic metal coated on the microstructures. Those eddy currents heat the metal and thereby enable localized heating of the tumor to therapeutic temperatures to occur.

The foregoing only touches the myriad ways in which metal clad lipid microstructures can be usefully employed.

The metal clad lipid microstructures can be produced by the procedures set forth in the following examples.

EXAMPLE 1

A dispersion of diacetylenic lipid vesicles in an agueous solution was prepared. Unpolymerized tubules at a concentration of 4 mg lipid/mL were thermally grown by raising the vesicular dispersion above the chain melting temperature of the diacetylenic lipids followed by slow cooling to just below that melting temperature. The average length of the tubules so produced was approximately thirty microns. XD2408 palladium chloride/tin chloride (Pd/Sn) colloidal activator (MacDermid Co., Waterbury, Conn.) was used as received. MaCuplex 9340 hypophosphite-reduced electroless nickel plating bath was made up from J-60 and J-61 concentrates as prescribed by the MacDermid Co. All solutions in this and other examples were prepared with distilled, deionized water.

In a polypropylene centrifuge vial, approximately 1 mL of the agueous tubule dispersion was combined with an equal volume of the Pd/Sn colloid and gently mixed for two minutes. After centrifugation at 13,000 rpm for three minutes at room temperature, the supernatant liguid was drawn off and the compressed pellet of tubules was resuspended in clean water. At this point, the tubules were distinctly brown (the color of the colloid). No leaching of the brown color into the solution was observed, indicating strong binding of the colloid to the tubules. Thereafter, the colloid treated tubule suspension was mixed with a large excess of the previously prepared electroless nickel plating bath.

After two minutes, rapid gas evolution was observed accompanied by a rapid change in the color of the dispersion from brown to black. It is known that hydrogen ($H_2$) gas is produced when plating occurs in a nickel or copper plating electroless bath. The bubbles therefore indicated that nickel plating had occurred. The reaction was then quenched by repeated centrifugation and resuspension in clean water.

The tubules were examined under a optical microscope with brightfield illumination. A dense, opaque, uniform black coating was observed on the surface of the tubules, indicative of an electroless nickel deposit. In contrast, the initial white lipid dispersion (i.e., the lipid dispersion before being mixed with the electroless plating solutions) is essentially invisible under brightfield illumination. The average length of the black coated tubules was approximately ten microns, considerably shorter than the typical distribution of lengths observed prior to metalization. The shorter length of the metal-coated tubules is attributed to the mechanical stress on the tubules from the centrifugation and resuspension procedures.

The identity of the deposit as nickel was confirmed using a standard qualitative procedure. In that procedure, the metal coating was first leached from the tubules using concentrated nitric acid. The leach solution was then neutralized with sodium hydroxide to pH 7. Solid sodium dimethylglyoximate (dmg) was added to the neutralized solution until the solution became pink due to formation of nickel dimethylglyoximate, $Ni(dmg)_2$.

The tubules were examined in a transmission electron microscope (TEM) both before and after the tubules were subjected to the electroless nickel plating bath. Before the tubules were plated with nickel, the TEM showed a relatively uniform attachment to the tubules of small, electron opaque particles. From the size of those particles (approximately 5nm to 25nm), it was concluded that the particles were colloidal Pd/Sn sensitizer particles that were bound to the lipid microstructure. After being subjected to the electroless plating bath, the nickel-plated tubules were observed to have an even, thin, fine grained metallic coating.

The placement of a small (less than $10^3$ gauss) magnet in the vicinity of the nickel-coated tubules attracted the tubules to the magnet. The tubules quickly followed the movement of the magnet without a discernible time lag, thereby indicating that the metallic deposit on the tubules was ferromagnetic.

EXAMPLE 2

A dispersion of tubules, was prepared at a concentration of 0.7 mg/mL by the solvent growth method cited above. The procedure for coating the tubules with nickel was identical to that employed in Example 1 with the exception that solvent-grown, rather than thermally-grown, tubules were employed. As in Example 1, the electroless plating procedure produced a black dispersion. Optical and electron microscopy showed the presence of a thin, metallic coating on the surface of the tubules.

EXAMPLE 3

Some of the unused white, solvent grown umpolymerized tubules obtained at tee beginning of the Example 2 procedure were exposed to $7.0 \times 10^6$ rad of gamma radiation. That radiation initiated polymerization of the irradiated tubules and caused the dispersed tubules to turn red. The polymerized tubules were then subjected to the electroless nickel plating procedure of Example 1 (i.e. Pd/Sn colloid treatment followed by immersion in the electroless nickel plating bath). The red tubules turned brown after treatment with the Pd/Sn colloid and then turned black after being metal coated in the nickel plating bath. Examination of the black lipid microstructures by brightfield optical microscopy confirmed the presence of a black metallic coating over the lipid surfaces. By employing a small magnet as in Example 1, it was established that the metal coat was magnetic.

EXAMPLE 4

A sac of Spectrapor 12,000–14,000 molecular weight cut-off dialysis tubing (Spectrm Medical Industries, Los Angeles, Calif.) containing 1 mL of a solution of unpolymerized solvent-grown tubules (average length 40 to 200 microns depending on batch) and 5 mL of XD 2408 Pd/Sn colloidal activator (MacDermid) was immersed in one liter of 0.1 M HCl and continuously stirred for four hours. The contents of the sac were then reduced to about one-fourth of its original volume by filtration through a 0.22 micron Millipore filter. The colloid treated tubules were then subjected to a Stabuff 500 (Stapleton Co., Long Beach, Calif.) electroless nickel plating bath which had been prepared as directed by the manufacturer. The plating reaction was quenched by pouring the tubule-nickel plating bath mixture into a large volume of water. The metal plated tubules wee then concentrated by filtration as above.

Examination of the metal plated lipid tubules with an optical microscope showed the length distribution of those tubules to be centered about 30 to 70 microns, depending on the starting batch. In contrast to the average 10 micron length of the tubules obtained when centrifugation was used, the longer length of these tubules is attributed to the lower mechanical stress exerted on the tubules in the dialysis and filtration procedure. The dialysis and filtration procedure appears to be more effective than the centrifugation procedure in preserving the initial aspect ratio (length to radius) of the lipid microstructures.

The nickel coated tubules were examined by X-ray fluorescence line scan in a scanning electron microscope (SEM) equipped with an energy dispersive X-ray spectrometer. The absence of electrical charging of the tubules in the electron beam indicated that the tubules were coated with an electrically conductive substance. The response of the X-ray emission line scan indicated that nickel was detected only when the electron beam moved across the metalized tubules. A back-scattered electron image of the nickel coated tubules indicated the presence on the microstructures of a uniform metal coat which was notable for its evenness.

EXAMPLE 5

A dispersion of unpolymerized tubules and helices was solvent grown in the manner previously described herein. Metex 9027 electroless copper plating bath wa prepared in accordance with the directions of the manufacturer (MacDermid Co.).

Metalization of tubules and helices was accomplished using the Example 4 procedure with substitution of the Metex 9027 copper plating bath for the nickel plating bath. After subjecting the colloid treated tubules and helices to the electroless copper plating bath for three minutes, gas bubbling became evident. The reaction was thereupon quenched as in the Example 4 procedure.

The initially white dispersion of lipids had become copper-brown in color. Inspection by brightfield optical microscopy revealed the presence of a uniform, opaque coat on the surfaces of the tubular and helical microstructures. The thermal stability of the coated microstructures was investigated using an optical microscope with a hot stage attachment. The copper coated lipid microstructure remained intact when subjected for 20 minutes or more to temperatures slightly above 40° C. (The chain melting temperature for the $DC_{23}PC$ lipid is 43° C.) Even when subjected to a temperature of 210° C. for two minutes, the copper coated lipid microstructures remained intact.

When the metal coated microstructures were examined in the SEM, the secondary election image clearly showed the presence of a uniform metallic coat on both tubules and helices. Examination by X-ray fluorescence line scanning confirmed the presence of elemental copper on the microstructures. Back-scattered electron and specimen current maps were also used to establish the presence of a metallic coat on the microstructures.

EXAMPLE 6

Some of the nickel coated tubules obtained at the end of the Example 2 procedure were immersed in the Metex 9027 electroless copper plating bath prepared in Example 5. The evolution of gas ($H_2$) bubbles indicated the onset of copper deposition. The reaction was quenched and the tubules were concentrated by centrifugation as described in Example 1.

Examination of the tubules by optical microscopy revealed the presence of both black (nickel) and brown (copper) on the same microstructure. X-ray fluorescence mapping of the microstructure surfaces, using the SEM, confirmed the presence of both copper and nickel on the microstructures. This experiment demonstrated the feasibility of using the initially metalized microstructures as substrates for subsequent processing.

EXAMPLE 7

Cataposit 44 Pd/Sn colloidal activator was prepared from Cataposit 44 concentrate and solid Cataprep 404 in accordance with the directions of the manufacturer (Shipley Co., Newton, Mass.). An electroless copper plating bath was prepared from 328 A and 328Q stock solutions as prescribed by the Shipley Company which had supplied those materials.

Metalization of a portion of the unused solvent-grown dispersion of tubules and helices obtained at the start of the Example 5 procedure was accomplished using a simulation of the Example 5 procedure with the substitution of the Shipley colloid and the Shipley copper plating bath for the MacDermid analogues. A plating of copper on the microstructures, similar to that produced in Example 5 was obtained. The presence of a metallic deposit on the microstructures was confirmed by optical and electron microscopy.

EXAMPLE 8

The Example 7 procedure for lipid microstructure metalization was employed using the MacDermid Metex 9027 electroless copper plating bath in place of the Shipley copper plating bath. Results similar to those produced by the Example 7 procedure were obtained.

EXAMPLE 9

The Example 7 procedure for metalization of lipid microstructures was employed using tubules formed from the diacetylenic lipid 1,2-bis(heptacosa-8,10-diynoyl)-sn-glycero-3-phosphocholine in place of those prepared with the $DC_{23}PC$ lipid. Copper deposition on the lipid microstructures was confirmed by brightfield optical microscopy.

EXAMPLE 10

Multilamellar vesicles were prepared as an aqueous dispersion from hydrogenated soy lecithin (American Lecithin Co., Atlanta, Ga.). That substance is a non-diacetylenic phosphocholine lipid. The procedure for the preparation of that aqueous dispersion is described in the previously cited article by Paul Yager and Paul E. Schoen published in 1984 in the "Journal of Molecular Crystals And Liquid Crystals", vol 106, pp 371-381. Those non diacetylenic lipid vesicles were metalized by the Example 1 procedure. A grey black coating of nickel was produced on those lipid microstructures. The presence of the nickel coating was confirmed by examination of the grey-black microstructures under brightfield illumination with an optical microscope.

EXAMPLE 11

Some of the unused copper-plated tubules from Example 7 were dehydrated by exchanging into acetone. The metalized microstructures were allowed to settle to the bottom of the container, the aqueous solution was pipetted off and the tubules resuspended in acetone. EPON 828 epoxy was prepared using a 1,3-diaminobenzene crosslinker as directed by the manufacturer (Shell Chemical Co.). A concentrated dispersion of the copper-coated tubules was added, with gentle mixing, to the epoxy, the ratio of tubules to epoxy was about 1% by volume. The resulting dark brown epoxy/tubule composite mixture was poured into a rectangular mold and the tubules were flow-aligned along the long axis of the mold. The composite was cured for 24 hours while in a vacuum. The composite was sliced perpendicular to the long axis and then placed in an RF (radio frequency) plasma etcher so that the aligned tubules were oriented vertically. The composite was etched in an oxygen plasma for six hours to remove the epoxy from around the tubules. Examination by SEM (scanning electron microscope) revealed copper-coated tubules protruding vertically from the epoxy substrate.

EXAMPLE 12

Nickel-plated tubules were prepared as described in Example 4 with the exception that the J60/J61 electroless nickel plating bath (MacDermid Co.) was substituted for the Stabuff 500 bath, and that the time of exposure of the colloid treated tubules to the plating bath was varied from one to six minutes. The presence of a nickel coat on the tubules was confirmed by optical microscopy.

EXAMPLE 13

The nickel-coated tubules prepared at various plating times as described in Example 12 were dehydrated and embedded in epoxy according to the procedure of Example 11, with the exception that a flat-plate ceramic magnet was used to align the microstructures an the epoxy was cured at room temperature. The composites were sectioned, using a microtome, into 40 nm thick slices, cut perpendicular to the axis of tubule alignment. Examination of the composites by SEM indicated that only tubules plated for more than about two minutes remained intact during the dehydration/embedding/sectioning procedure. Cross-sectional views of the tubules showed metal coats on both the inner and outer surfaces of the cylinders. The thickness of the coats ranged between 17 nm and 45 nm, and increased monotonically with the plating time. Epoxy was clearly present throughout the interior of the tubules.

Instead of employing an epoxy for the matrix, the tubules can be embedded in any of a wide variety of materials. Polyurethane, for example, is a suitable material for employment as the matrix for embedding the tubules.

THE FLOW DIAGRAM

Referring now to the FIG. 1 flow diagram, the procedure for producing metal clad lipid microstructures starts with the step of producing the lipid microstructures in forms which may be helical, tubular, or spheroidal. For simplicity the steps of washing, rinsing, and concentrating the lipid microstructures have been omitted from the flow diagram. Where it is desired to enhance the thermal, chemical or mechanical stability of the lipid, the lipid microstructures are irradiated with energy sufficient to cause polymerization of the lipids, such as by deep UV light, X-rays, gamma rays, or electrons. The lipid polymerization step is optional and may be skipped. By following the remaining steps, metal clad lipid microstructures will be produced. To indicate that the polymerization step is optional, that step is shown in FIG. 1 in a broken line box. Whether or not the optional step is used, the next step is to cause a catalyst precursor to be absorbed on the microstructures. Those microstructures are then subjected to the action of an electroless metal plating bath that deposits metal on the surfaces of the microstructures.

In view of the obvious changes that can be made in the foregoing procedures, it is intended that the invention not be restricted to the precise examples here described. Rather, it is intended that the scope of the invention be construed in accordance with the appended claims, having due regard for changes that are obvious to those skilled in the metal plating art or in the associated field of surface chemistry.

We claim:

1. A self-assembling lipid microstructure presensitized on its exposed surfaces with a catalyst precursor and clad with an adherent electrically conductive metal.

2. A self-assembling lipid microstructure presensitized on its exposed surfaces with a catalyst and clad with an adherent electrically non-magnetic metal.

3. A self-assembling lipid microstructure presensitized on its exposed surfaces with a catalyst precursor and clad with an adherent ferromagnetic, electrically conductive metal.

4. A helical self-assembling lipid microstructure presensitized on its exposed surfaces with a catalyst precursor and having an adherent metal coat deposited thereon.

5. A tubular self-assembling lipid microstructure presensitized on its exposed surfaces with a catalyst precursor and having an adherent metal coat deposited thereon.

6. A hollow cylindrical self-assembling lipid microstructure presensitized on its inner and outer surfaces with a catalyst precursor and having an adherent metal deposited thereon.

7. A self-assembling lipid vesicle microstructure presensitized on its exposed surfaces with a catalyst precursor and having an adherent metal coat deposited thereon.

8. A composite material comprising metal-coated self-assembling lipid microstructure embedded in a polymer matrix.

9. The composite material according to claim 8, wherein the polymer of the matrix is comprised of an epoxy.

10. The composite material according to claim 8, wherein the polymer of the matrix is comprised of polyurethane.

11. The composite material according to claim 8, wherein the metal coated microstructures comprise elongate longitudinally aligned tubules.

12. A method of coating a self-assembling lipid microstructure with an adherent electrically conductive metal, comprising the steps of
    (1) producing a lipid microstructure,
    (2) causing a catalyst precursor to adhere to the surface of the self-assembling lipid microstructure, and
    (3) plating a metal or metal alloy onto the catalyst treated microstructure in an electroless plating bath.

13. The method according to claim 12, including the further step of
    (4) irradiating the self-assembling lipid microstructure prior to step 2 with energy sufficient to cause polymerization of the self-assembling lipid.

14. The method according to claim 13, including the additional step of
    (5) coating the irradiated polymerized self-assembling lipid microstructure with a plating bath pre-activator before coating those microstructures with the catalyst precursor.

15. The method according to claim 12, wherein the catalyst precursor in step 2 contains palladium.

16. The method according to claim 12, wherein the catalyst precursor in step 2 is a colloid containing palladium and tin.

17. The method according to claim 12, wherein the plating bath of step 3 is a solution of a reducible metal complex.

18. The method according to claim 12, wherein the plating bath in step 3 is an electroless copper plating bath.

19. The method according to claim 12, wherein the plating bath in step 3 is an electroless nickel plating bath.

20. The method according to claim 19, wherein the plating bath is an alkaline electroless nickel plating bath whereby the metal deposited on the microstructure is ferromagnetic.

21. The method according to claim 19, herein the plating bath is an acid electroless nickel plating bath whereby the metal deposited on the microstructure is non-magnetic.

22. The microstructure according to claims 1, 2, 3, 4, 5, 6, 7, 8 or 12 wherein the self-assembling lipid comprises a phospholipid.

23. The microstructure according to claims 1, 2, 3, 4, 5, 6, 7, 8 or 12 wherein the self-assembling lipid comprises a diacetylenic phospholipid.

24. The composite material according to claim 11 wherein the aligned tubules protrude vertically from the polymer matrix.

* * * * *